United States Patent [19]

Tajima

[11] Patent Number: 4,963,358

[45] Date of Patent: Oct. 16, 1990

[54] AGENT FOR INHIBITING PROLIFERATION OF HUMAN MALIGNANT TUMOR CELLS

[75] Inventor: Tomoyuki Tajima, Ichikawa, Japan

[73] Assignees: Koken Ltd.; Tadakatsu Oishi; Youichiro Nagasu; Hisao Yamaguchi, all of Japan

[21] Appl. No.: 282,458

[22] Filed: Dec. 9, 1988

Related U.S. Application Data

[63] Continuation of Ser. No. 785,229, Oct. 7, 1985, Pat. No. 4,810,495, which is a continuation-in-part of Ser. No. 471,854, Mar. 3, 1983, abandoned.

[30] Foreign Application Priority Data

Aug. 20, 1982 [JP] Japan ................................ 57-143340

[51] Int. Cl.$^5$ ......................... A61K 35/12; C12P 1/00
[52] U.S. Cl. ..................................... 424/548; 435/41; 435/240.2; 424/551; 424/557; 424/558; 424/573
[58] Field of Search .................. 424/95; 435/41, 240.2

[56] References Cited

U.S. PATENT DOCUMENTS

| | | | |
|---|---|---|---|
| 4,349,541 | 9/1982 | Takeda et al. | 424/95 |
| 4,415,553 | 11/1983 | Zhabilov et al. | 424/95 |
| 4,559,228 | 12/1985 | Delatorre | 424/95 X |
| 4,588,587 | 5/1986 | Gasic | 424/95 |
| 4,595,657 | 6/1986 | Tajima | 435/41 |

OTHER PUBLICATIONS

M. Spencer et al., *Cancer Research*, Part 2, vol. 25(4):943 (May 1965).

*Primary Examiner*—Alan L. Rotman
*Attorney, Agent, or Firm*—Lowe, Price, LeBlanc, Becker & Shur

[57] ABSTRACT

An agent for inhibiting proliferation of human malignant tumor cells is obtained by culturing the human malignant tumor cells in a medium and removing the malignant tumor cells from the cultured medium.

12 Claims, 17 Drawing Sheets

F I G. 11
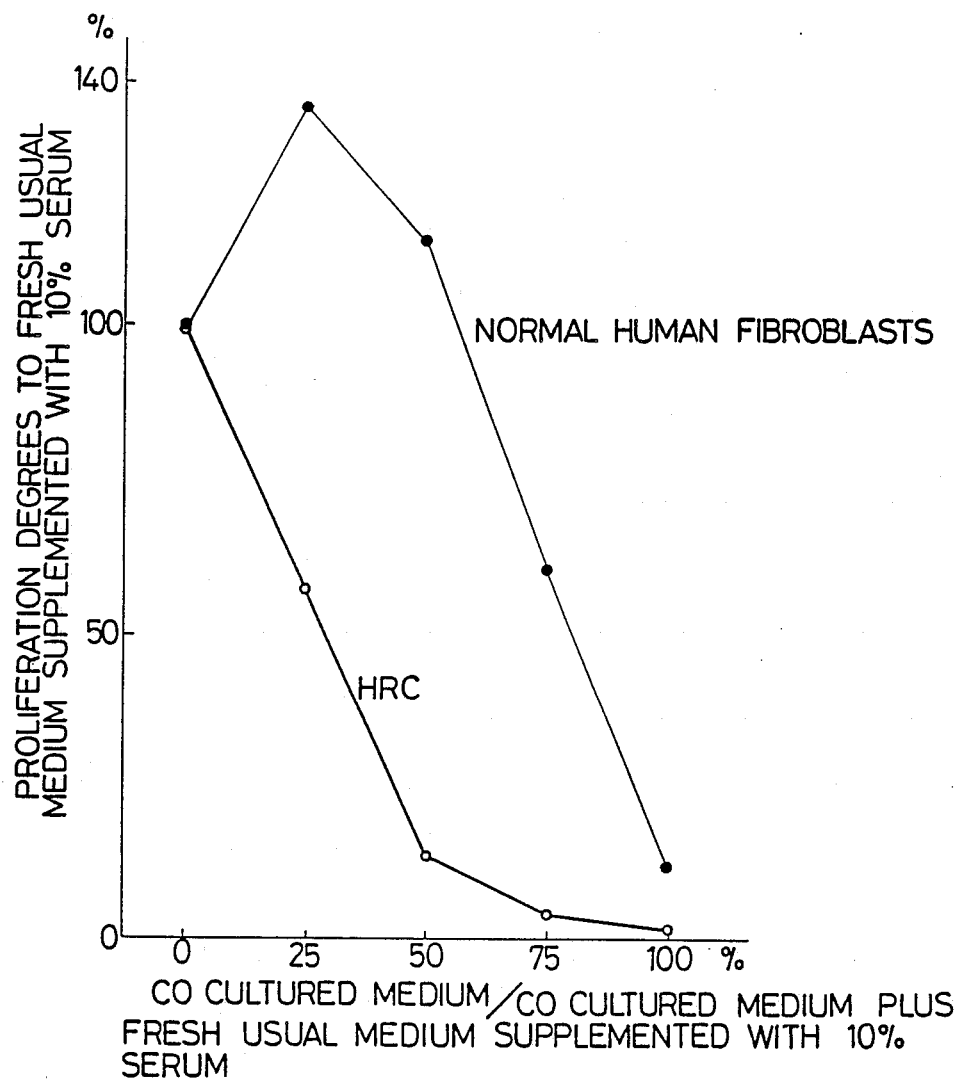

AGENT FOR INHIBITING PROLIFERATION OF HUMAN MALIGNANT TUMOR CELLS

This is a continuation of application Ser. No. 785,229, filed Oct. 7, 1985, now U.S. Pat. No. 4,810,495, which is a continuation-in-part of application Ser. No. 471,854, filed Mar. 3, 1983, now abandoned.

BACKGROUND OF THE INVENTION

The present invention relates to an agent for inhibiting the proliferation of human malignant tumor cells.

SUMMARY OF THE INVENTION

It is a first object of the present invention to provide an agent for inhibiting the proliferation of human malignant tumor cells which is obtained by culturing the human malignant tumor cells and then subjecting the cultured media to extraction so as to remove the malignant tumor cells therefrom. This inhibitor can inhibit the proliferation of human tumor cells and has a cytolytic effect thereon. The inhibitor according to the present invention is a substance having a low molecular weight, which may pass through a filter such as a YM2 or UM05 filter manufactured by Amicon, which is capable of passing a substance having a molecular weight of 500 or 1,000 therethrough. This substance obtained by extraction may show some inhibitive effect on growth of normal cells; however, its ability to inhibit the proliferation of malignant tumor cells is remarkably greater than that in respect of normal cells. Furthermore, no cytolytic effect against normal cells can be observed. Therefore, the inhibitor according to the present invention may show few of the side effects which often appear with conventional anti-tumor agents.

It is a second object of the present invention to provide an agent for inhibiting the proliferation of human lung carcinoma cells.

It is a third object of the present invention to provide an agent for inhibiting the proliferation of human malignant tumor cells which is obtained by culturing the malignant tumor cells in a growth medium which is a synthetic medium supplemented with 10% new born calf serum.

It is a fourth object of the present invention to provide an agent for inhibiting the proliferation of human malignant tumor cells which is obtained using Basal Medium Eagle (Ref; Eagle, H.: Science, 122,501–504, 1955) as a synthetic growth medium.

It is a fifth object of the present invention to provide an agent for inhibiting the proliferation of human malignant tumor cells which is obtained by culturing the malignant tumor cells in a growth medium which is a synthetic medium supplemented with 10% new born calf serum.

It is a sixth object of the present invention to provide an agent for inhibiting the proliferation of human malignant tumor cells which is obtained using RPMI1640 as a synthetic medium (Ref; Moore, G. E.:J.A.M.A., 199:519–524, 1967).

It is a seventh object or the present invention to provide an agent for inhibiting the proliferation of human malignant tumor cells which is obtained by growing the malignant tumor cells in a growth medium, incubating the proliferated malignant tumor cells in an extraction medium which contains no serum, and removing the malignant tumor cells from the extraction medium after incubation.

It is an eighth object of the present invention to provide an agent for inhibiting the proliferation of human malignant tumor cells which is obtained using a synthetic medium as an extracting medium.

It is a ninth object of the present invention to provide an agent for inhibiting the proliferation of human malignant tumor cells which is obtained using Basal Medium Eagle (Ref; Eagle, H.:Science, 122, 501–504, 1955) as a synthetic extraction medium.

It is a tenth object of the present invention to provide an agent for inhibiting the proliferation of human malignant tumor cells which is obtained by extracting the malignant tumor cells using a molecular sieve capable of passing substances having molecular weights of 500 or larger therethrough.

A substance obtained by extraction from a medium after the incubation of co-cultured human malignant tumor cells and human normal cells provides an effect similar to that obtainable from cultured human malignant tumor cells alone. Selection of an appropriate ratio of a co-cultured medium to a fresh normal medium can promote the proliferation of normal cells and decrease the proliferation of malignant tumor cells to a remarkable extent.

It is, therefore, an eleventh object of the present invention to provide an agent for inhibiting the proliferation of human malignant tumor cells which is obtained by co-culturing human malignant tumor cells with normal human fibroblasts and then removing the malignant tumor cells from the medium by extraction.

It is a twelfth object of the present invention to provide an agent for inhibiting the proliferation of human malignant tumor cells which is obtained from a co-culture system in which the normal human fibroblasts are normal human diploid skin fibroblasts.

It is a thirteenth object of the present invention to provide an agent for inhibiting the proliferation of human malignant tumor cells which is obtained from a co-culture system using a synthetic medium supplemented with 10% new born calf serum.

BRIEF DESCRIPTION OF THE DRAWINGS

FIG. 11 is a graph showing the proliferation of normal cells and carcinoma cells in media comprising various ratios of a co-cultured medium to a fresh normal medium;

Figure 1:
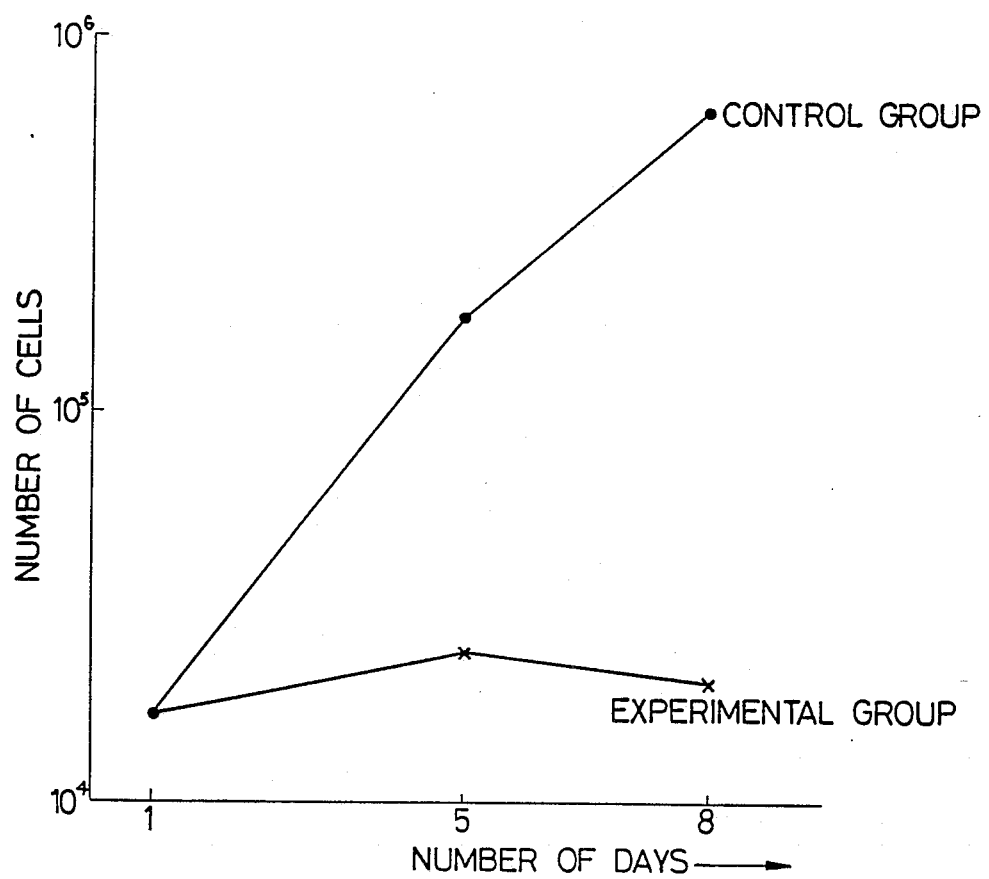
FIG. 1 is a graph showing the proliferation of established cell lines HRC originated from a human renal carcinoma in each of media.

Table 1 is a comparison of effects on cell proliferation of fractions of various molecular weight.

DETAILED DESCRIPTION OF THE PREFERRED EMBODIMENTS

Experiment 1

(1) Cells Used as Experimental Materials

As experimental materials for cells are employed various established cell lines separated from human tumor cells. The established cell lines of human carcinoma origin include, respectively, five different cells: HRC originated from a human renal carcinoma, MK from a human gastric carcinoma, PC-1 from a human lung carcinoma, KB from a carcinoma of the human oral cavity, and HMS from a human myogenic sarcoma.

(2) Culture

As growth media are employed Basal Medium Eagle (Ref; Eagle, H.: Science, 122, 501–504, 1955) (BME) or Eagle Minimal Essential Medium Supplemented with 10% new born calf serum and RPMI1640 supplemented with 5% new born calf serum. As an extracting medium is used BME with no serum supplement.

The culture may be carried out by proliferating human malignant tumor cells in a growth medium to a degree at which the growth medium is saturated with the human malignant tumor cells, culture conditions are as follows, 100 ml of serum containing media (PH 7.2–7.4) are inoculated with $3-5 \times 10^7$ cells of these established lined cells originated from various human malignant tumors; then, they are cultivated in a roller tube, posseses about 790 $cm^2$ of culture area at 37° C., or 30–50 ml of these growth media innoculated by these lined cells in same concentrations, which are cultivated in a culture bottle posseses about 150 $cm^2$ culture area at 37° C. Open system for cell cultivation (cultured these cells in culture vessels in 5% $CO_2$ in air, 100% humidity at 37° C.) is often used for getting good condition for cell proliferation. And the medium is washed once to remove the serum. These cells may then be incubated in their entirety with an extracting medium at 37° C. for 3 or 4 days; alternatively $5 \times 10^7 - 1 \times 10^8$ of these lined cells collected from the cells proliferated herein above may be; inoculated into 50 ml of serum free media(PH 7.2–7.4) in a culture bottle posseses about 150 $cm^2$ culture area and then incubated as in usual passage generations at 37° C. for 3 or 4 days. This is followed by collection of the incubated medium.

(3) Partial Purification

The cultured medium is then filtered therethrough molecular sieves capable of passing therethrough substances with molecular weights of 10,000, 1,000 and 500, respectively, and the filtrate is collected.

(4) Assay of Inhibitor to Human Malignant Tumor Cells

Cells used for the assay are the five different cell lines used as experimental materials, and normal human diploid skin fibroblasts explanted from the trunk skin of a normal aged 63 (NAS 63).

The proliferation of cells is measured with reference to a growth curve and a dose response curve.

a. Growth Curve $1 \times 10^4 - 2 \times 10^4$ of cells is inoculated into a cultured medium which has been prepared by adding to a pre-filtered extraction medium the same composition and amount of glucose, amino acids and vitamins as in BME, and then supplementing the medium with 10% new born calf serum. The number of cells is counted daily or after a given period of culture.

b. Dose Response Curve

A cultured medium is mixed with a corresponding fresh medium in various amounts and a variety of nutrition is supplemented thereto in a similar manner as in the preparation for the growth curves. The number of cells is counted after a predetermined period of incubation.

(5) Experimental Results

FIGS. 1 to 5, respectively, show growth curves illustrating the daily variation in proliferation of various cells comprising the cultured medium.

For each experiment, the experimental group involves the use of a medium prepared by adding glucose, amino acids, vitamins and 10% serum as nutritive sources to an experimental group of various media obtained by ultrafiltration through an Amicon YM5 filter (M.W. $10^3$) of each cultured medium after the incubation of the respective malignant tumor cells. As a control is used fresh BME supplemented with nutritive sources as for the experimental group. The initial concentration of cells is $1 \times 10^4$ cells. In the first experiment, the results of which are shown in FIG. 1, a disk having a diameter of 35 mm is used, and in subsequent experiments the results which are shown in FIGS. 2 to 5 respectively, a disk having a diameter of 15 mm is used.

FIG. 1 shows the obtained results of an experiment conducted to determine the daily variation in the proliferation of established cell lines HRC originated from a human renal carcinoma. It is apparent from the experimental results that the experimental group containing a substance obtained by extraction of the medium incubated with human renal carcinoma cells HRC inhibits the proliferation of such cells, while the proliferation of such cells is recognized in the control group.

Figure 2A:
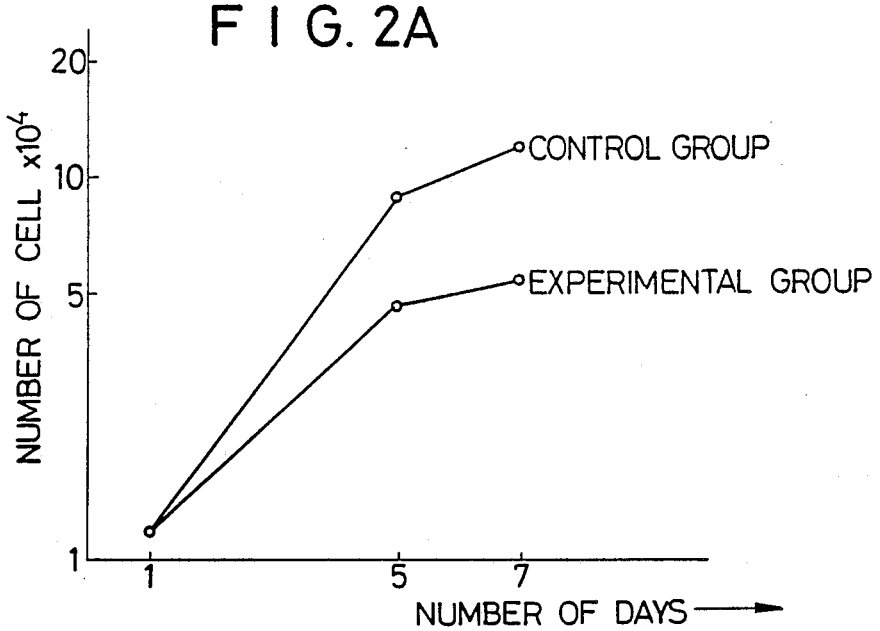
FIG. 2A is a graph showing the proliferation of normal human diploid skin fibroblasts NAS 63 in each of media.
Figure 2B:
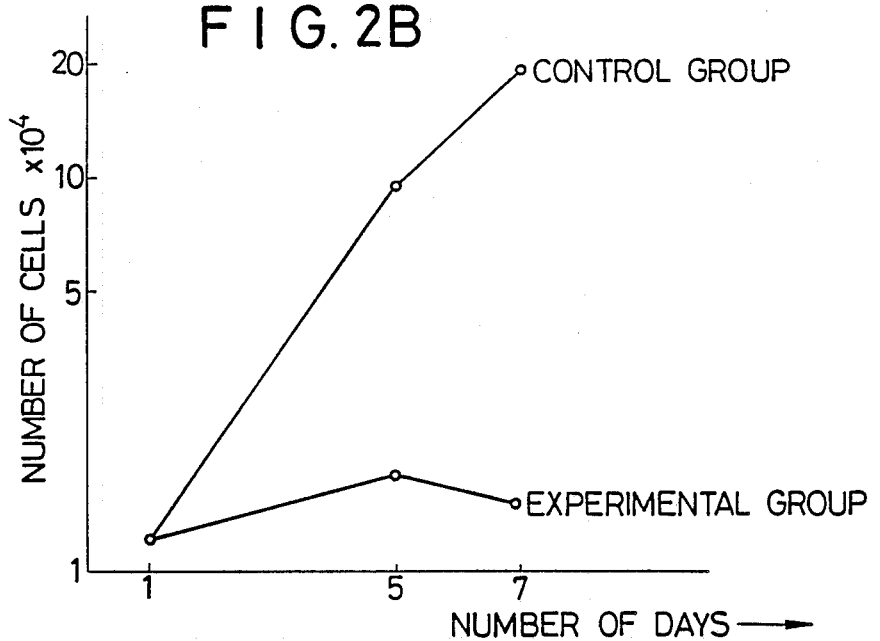
FIG. 2B is a graph showing the proliferation of established cell lines MK originated from a human gastric carcinoma in each of media.

FIG. 2A illustrates the daily variation in the proliferation of normal human diploid skin fibroblasts NAS 63, and FIG. 2B illustrates the same for human gastric carcinoma cells MK. In each experimental group, a medium is employed containing a substance obtained by extraction of a medium incubated with established human gastric carcinoma cell lines MK. The growth curves shown in FIGS. 2A and 2B, respectively, show that the experimental groups using the established human gastric carcinoma cell lines MK have an inhibitive effect on cell proliferation as compared to normal cells.

Figure 3:
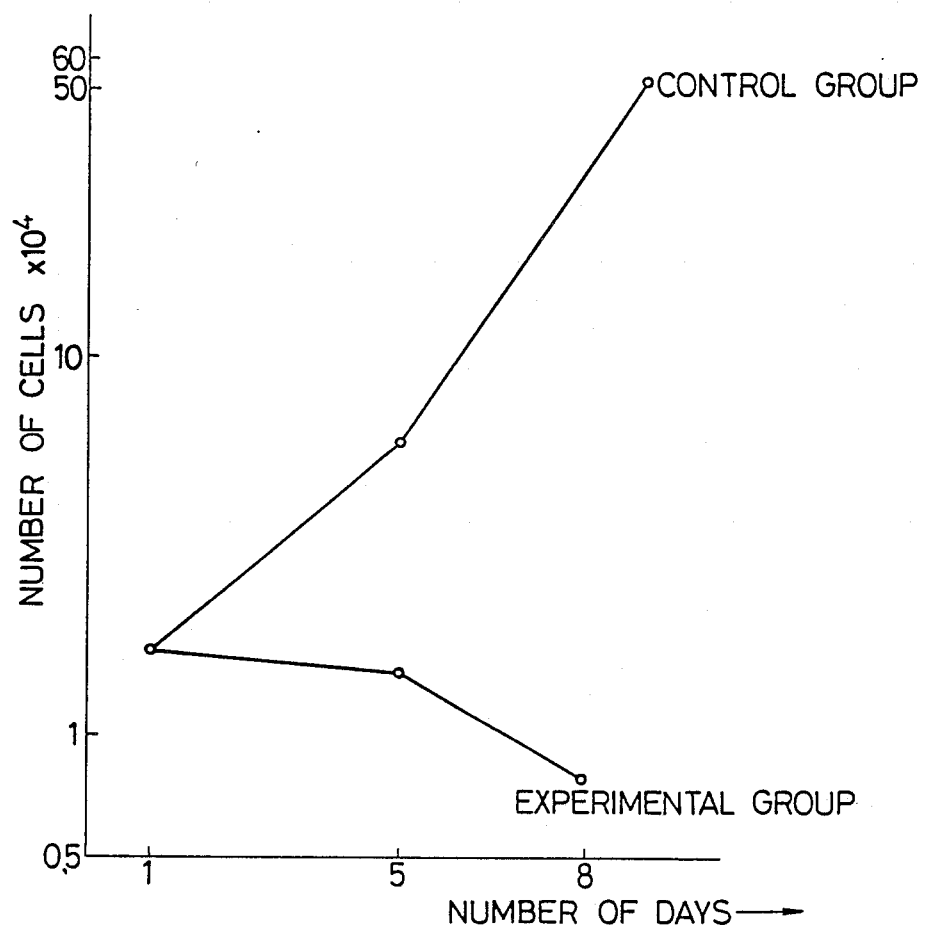
FIG. 3 is a graph showing the proliferation of established cell lines PC-1 originated from a human lung carcinoma in each of media.

FIG. 3 illustrates the daily variation in the proliferation of the established human lung carcinoma cell lines PC-1. The experimental results show a decrease in the number of cells in the experimental group containing a substance obtained by extraction of the medium incubated with the established human lung carcinoma cell lines PC-1, and demonstrates the cytolytic properties of the substance.

Figure 4:
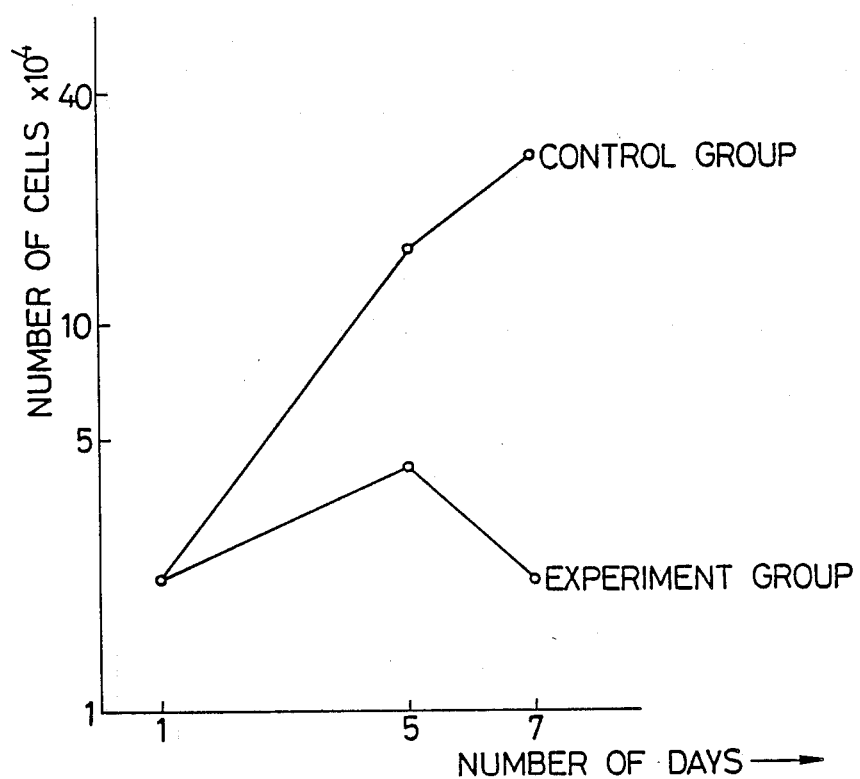
FIG. 4 is a graph showing the proliferation of established cell lines KB originated from a carcinoma of the human oral cavity in each of media.

FIG. 4 illustrates the daily variation in the proliferation of established cell lines KB originated from a carcinoma of the human oral cavity. In the experimental group containing a substance obtained by extraction of the medium incubated with established cell lines KB, it is found that the cells proliferate temporarily and then decline in number.

Figure 5:
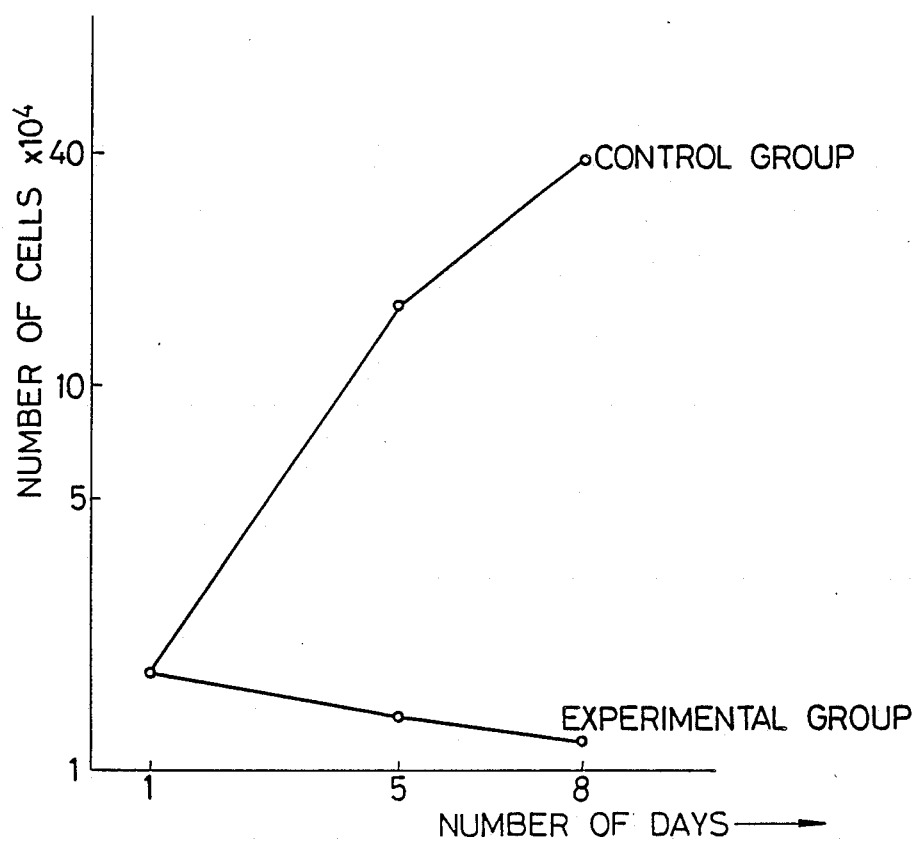
FIG. 5 is a graph showing the proliferation of established cell lines HMS originated from a human myogenic sarcoma in each of media.

FIG. 5 illustrates the daily variation in the proliferation of established human myogenic sarcoma cell lines HMS. In the experimental group containing a substance obtained by extraction of the medium incubated with established human myogenic sarcoma cell lines HMS, it is found that the number of cells decreases, demonstrating the cytolytic effect.

Figure 6:
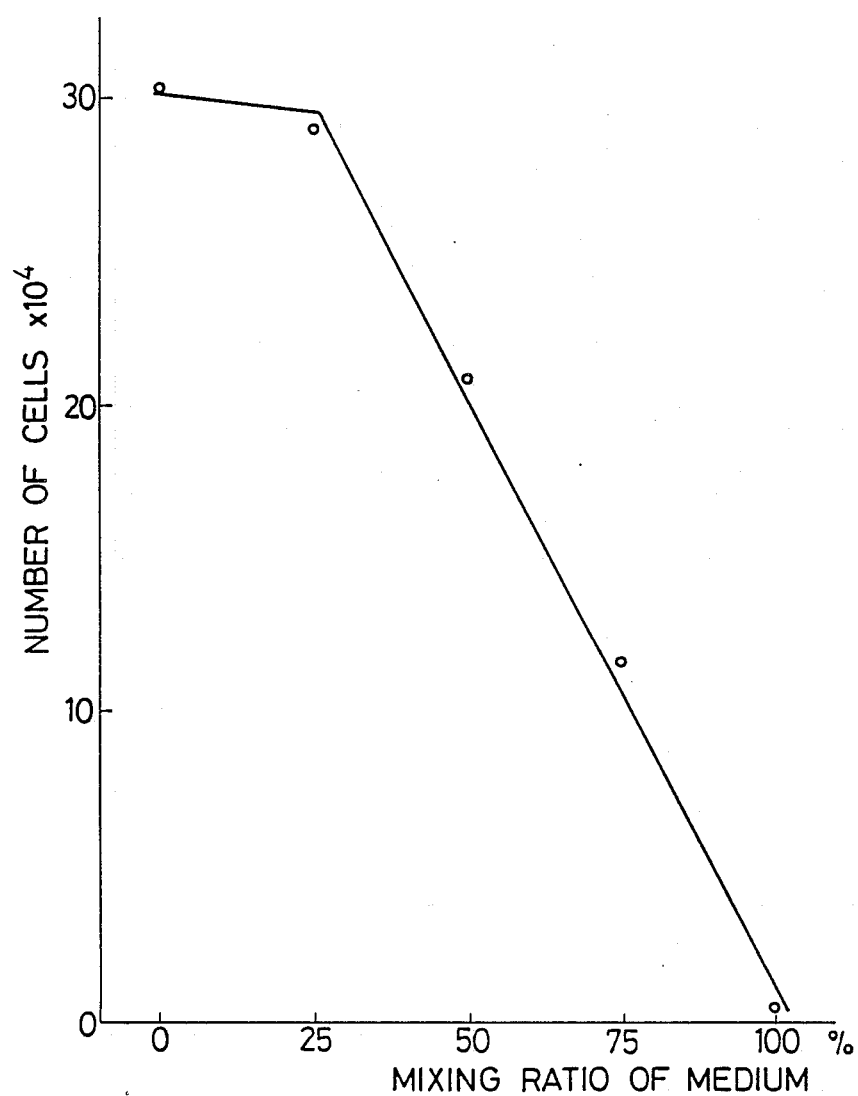
FIG. 6 is a graph showing dose responses of established cell lines HRC originated from human renal carcinoma for various ratios of a cultured medium to a fresh medium, the former medium being obtained by culturing established cell lines HRC originated from human renal carcinoma.
Figure 7:
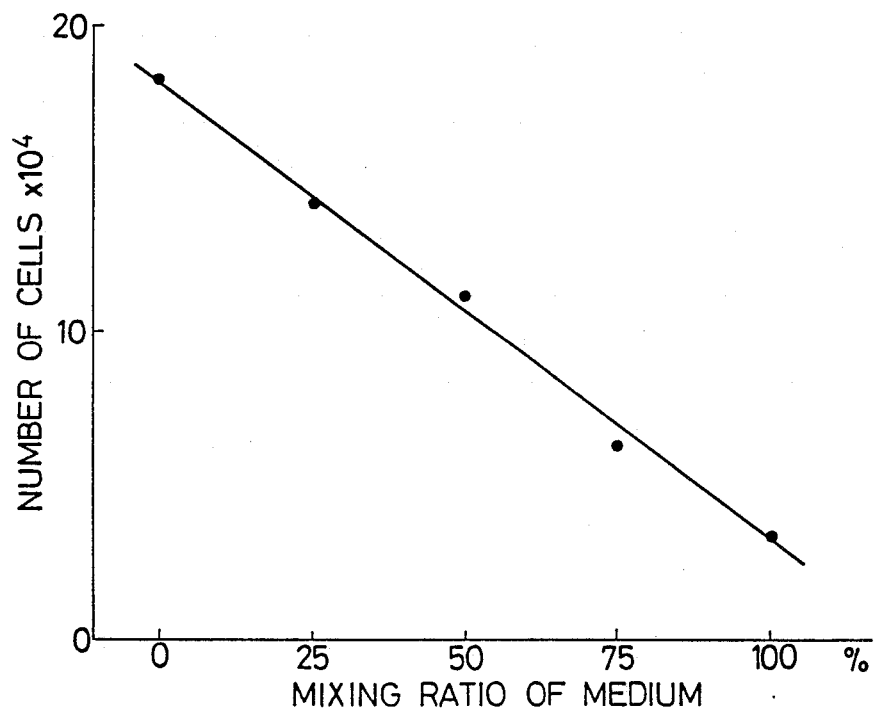
FIG. 7 is a graph showing dose responses of normal human diploid skin fibroblasts NAS 63 for each of the media used in FIG. 6.

FIGS. 6 and 7 show the results of experiments conducted to determine dose responses for various ratios of a fresh medium to a medium incubated with established cell lines HRC originated from the human renal carcinoma. FIG. 6 illustrates the dose response curves of the established human renal carcinoma cell lines HRC, and FIG. 7 illustrates those of normal human diploid skin fibroblasts NAS 63. In each experiment, after incubation, the culture medium used is passed through an Amicon YM2 filter capable of filtering substances with a molecular weight of 100. Each ratio (expressed as a percentage) is a ratio of an incubated medium to a sum of the incubated medium and a fresh medium. These figures indicate that the inhibitive effects on proliferation of established human renal carcinoma cell lines HRC, which is one of malignant tumors, are stronger than those in respect of normal cells in the incubated medium.

Table 1 shows a comparison of the effects on cell proliferation between fractions of different molecular weights obtained by ultrafiltration. In this comparison, normal human diploid skin fibroblasts NAS 63 and established human renal carcinoma cell lines HRC are employed.

In Table 1, symbols ①, ② and ③, respectively, indicate the number of each group. Groups ① and ② contain fractions having molecular weights of $10^3$ or lower which specifically show inhibitive and cytolytic effects against established human renal carcinoma cell lines. The fractions are shown to have some inhibitive influence on normal cells, too, but no cytolytic effect against normal cells can be seen by morphological observation.

TABLE 1

| Fractions | NAS 63 Cell ($\times 10^4$) numbers | % | HRS Cell ($\times 10^4$) numbers | % |
|---|---|---|---|---|
| Control | 6.30 | 100 | 21.14 | 100 |
| ① ≦ $10^3$ | 1.58 | 25 | 0.33 | 1.6 |
| ② ≦ $10^3$ | 1.72 | 27 | 0.31 | 1.5 |
| $10^3$ ≦ ③ ≦ 4 | 3.78 | 60 | 17.87 | 85 |

Experiment 2

(1) Cells Used as Experimental Materials

As experimental cell materials are used normal human diploid skin fibroblasts explanted from the trunk skin of males aged 53 and 63, respectively, and established cell lines originated from a human renal cell carcinoma gravity's tumor (HRC).

(2) Culture

As a medium is employed Basal Medium Eagle (BME) supplemented with 10% new born calf serum. Conditions for incubation are a closed system or a system open to the air containing 5% $CO_2$ and having a 100% humidity, and incubation is carried out at 37° C.

A combined or co-culture is conducted by first incubating human fibroblasts in the medium set forth hereinabove. When the culture vessel is fully covered with cells with no free surface area, established cell lines HRC from a human renal carcinoma is inoculated in the amount of $1-2 \times 10^7$ cells. The culture vessel used is a so-called Roux-bottle. The combined culture is then conducted by discharging the 10% new born calf serum from the Roux-bottle, and then using fresh BME either supplemented with 10% new born calf serum or with no serum added. The medium is incubated at 37° C. for 4 days followed by collection of the medium.

(3) Dialysis and Concentration

The collected medium is then placed in a Visking tube (a tube made of cellophane and conventionally used for dialysis) having its outer surface covered with polyethylene glycol, and is concentrated. Thereafter, dialysis is conducted with deionized 10 mM sodium bicarbonate.

(4) Assay of Inhibitor of the Proliferation of Carcinoma Cells

Carcinoma cells to be used for assay include established cell lines originated from a human renal carcinoma (HRC) and from a carcinoma of the human oral cavity (KB). Media used for assay include the collected medium and the dialyzed medium which are respectively added in turn to a fresh medium supplemented with a 10% new born calf serum in a plastic dish. Two different carcinoma cells comprising the established cell lines originated from a human renal cell carcinoma (HRC) and from a carcinoma of the human oral cavity (KB), and normal human fibroblasts are incubated in the media to measure their proliferation.

(5) Experimental Results

Figure 8:
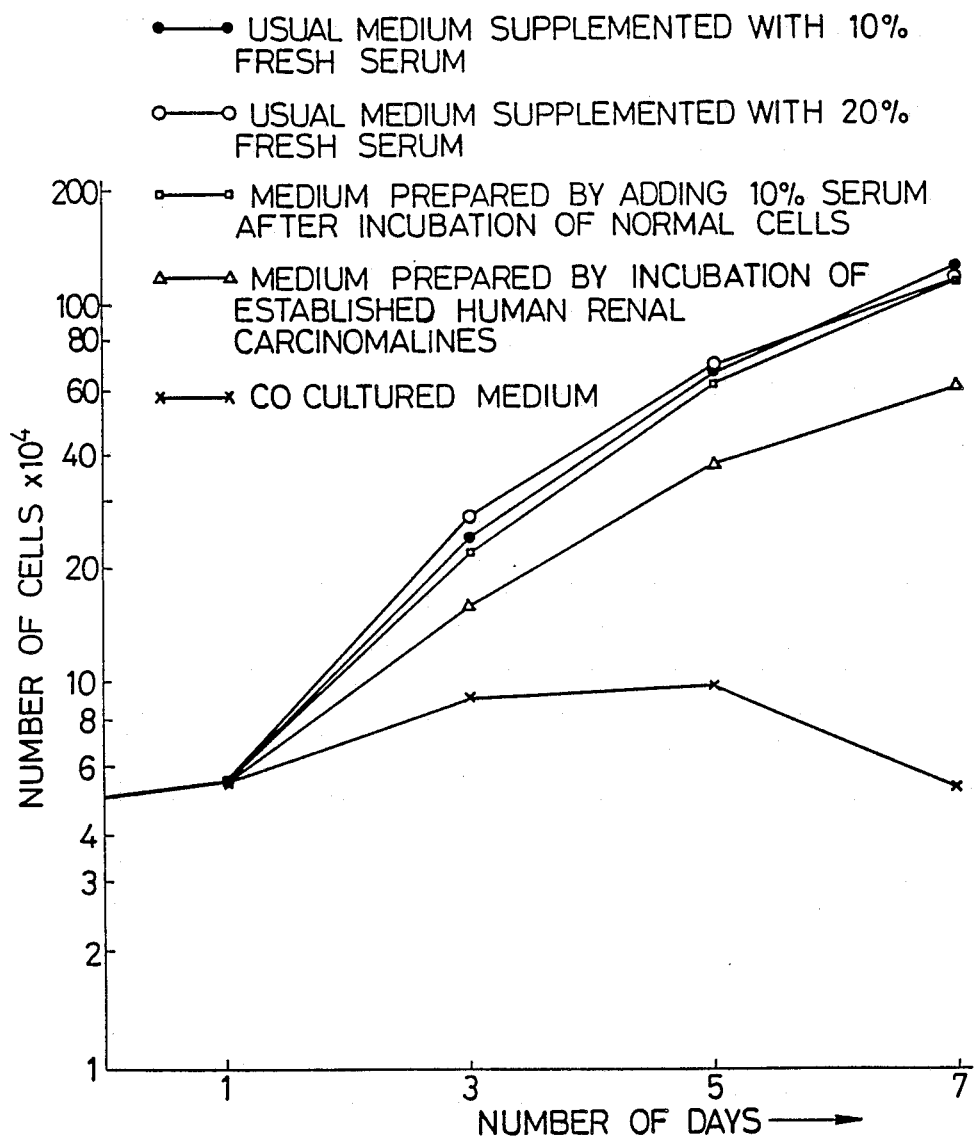
FIG. 8 is a graph showing the proliferation of carcinoma cells in each of media.

FIG. 8 shows proliferation curves indicating cell numbers of established human renal carcinoma cell lines HRC with respect to number of days of culture using various respective media, namely, a usual medium supplemented with 10% fresh serum, a usual medium supplemented with 20% fresh serum, a medium prepared by adding 10% serum after incubation of normal cells, a medium prepared by incubation of established human renal carcinoma cell lines, and a medium prepared by combined culture. The results indicate that only the incubation of the combined culture medium demonstrates inhibitive effects on proliferation and also demonstrates damage to the carcinoma cells.

Figure 9:
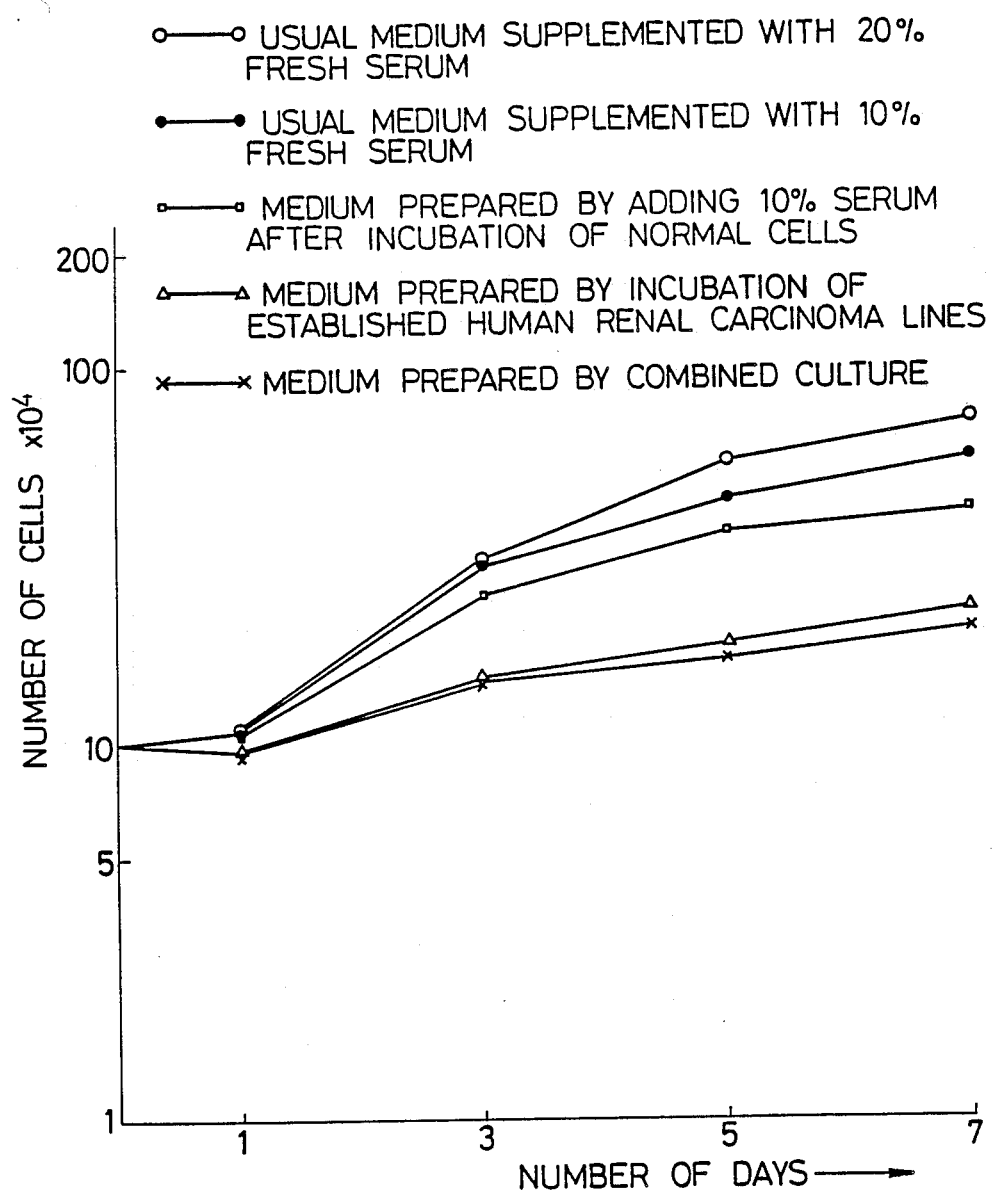
FIG. 9 is a graph showing the proliferation of normal cells in each of media.

FIG. 9 shows the results of an experiment which is conducted by incubating normal human fibroblasts in the various media used for the experiment whose results are shown in FIG. 1. In the co-cultured medium, a tendency toward proliferation is also seen in the increased number of cells with an increased number of days of culture in the co-cultured medium.

Figure 10:
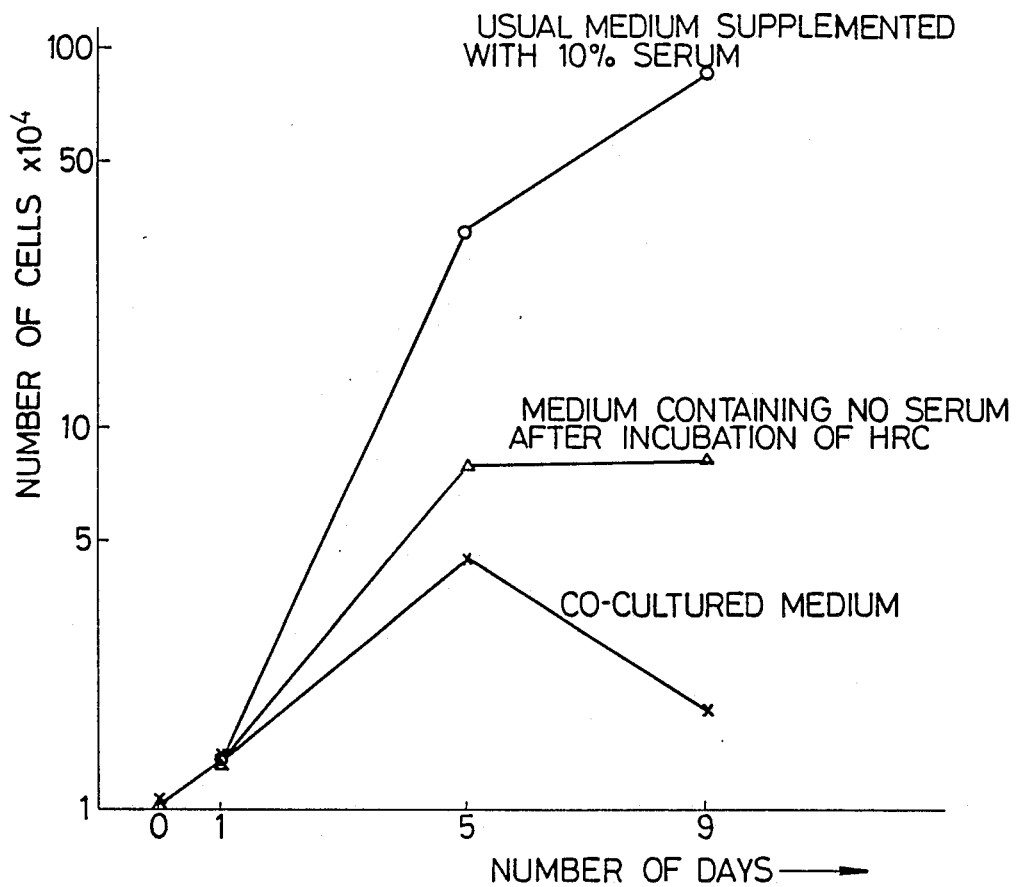
FIG. 10 is a graph showing the proliferation of carcinoma cells in a medium to which no serum is added.

FIG. 10 shows the results of experiments which are conducted using combined culture in a medium with no serum supplement and then incubating established human renal carcinoma cell lines HRC in a medium prepared by adding 10% fresh serum to the co-cultured serum-less medium, or in a usual medium supplemented with a 10% serum, or in a medium containing no serum after incubation of HRC. The results indicate that combined culture in a medium containing no serum can give similar effects. This means that the extraction of an agent for inhibiting the proliferation of human tumor cells may be effected smoothly without the presence of serum interfering in any way with this proliferation.

FIG. 11 indicates proliferation degrees of normal human fibroblasts and established human renal carcinoma cell lines HRC in media prepared by mixing the co-cultured media in varying percentage ratios thereof to the sum of the co-cultured medium and a fresh usual medium supplemented with 10% serum. The results show that normal cells proliferated in media of certain percentage ratios more than in a normal cell medium, and that the proliferation of tumor cells decreases in a logarithmical manner.

Figure 12:
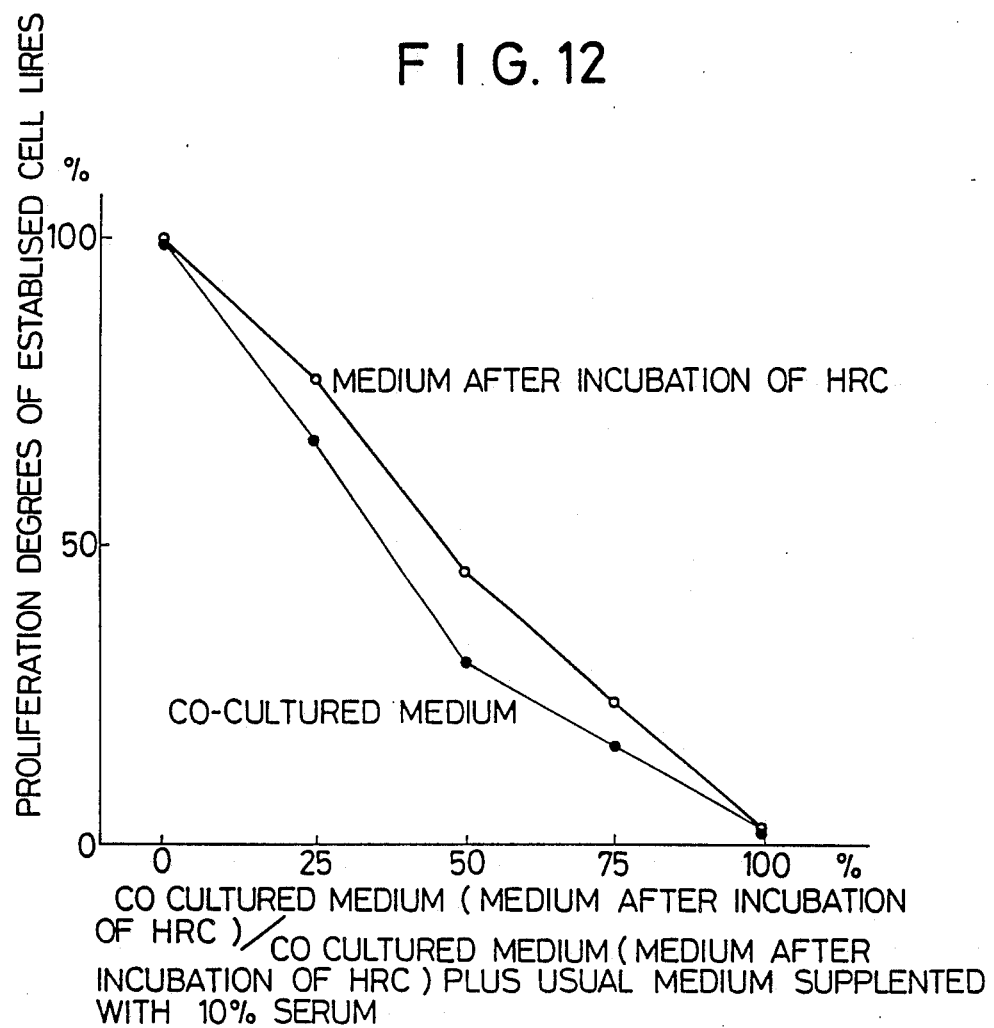
FIG. 12 is a graph showing the proliferation of carcinoma cells of different types in media comprising various ratios of a co-cultured medium to a fresh normal medium.

FIG. 12 indicates the respective proliferation degrees of established cell lines KB originated from a carcinoma of the human oral cavity in, respectively, a medium as described in FIG. 4 or a medium after incubation of HRC and in a co-cultured medium with a usual medium supplemented with 10% serum or in a medium after the incubation of HRC. The results indicate that, in the co-cultured media, the higher the ratio of the co-cultured medium used, the higher the degree of inhibition. This means that co-cultured media may contribute to the inhibition of the proliferation of tumor cells, and that inhibition may be caused by a substance obtained therefrom.

Figure 13:
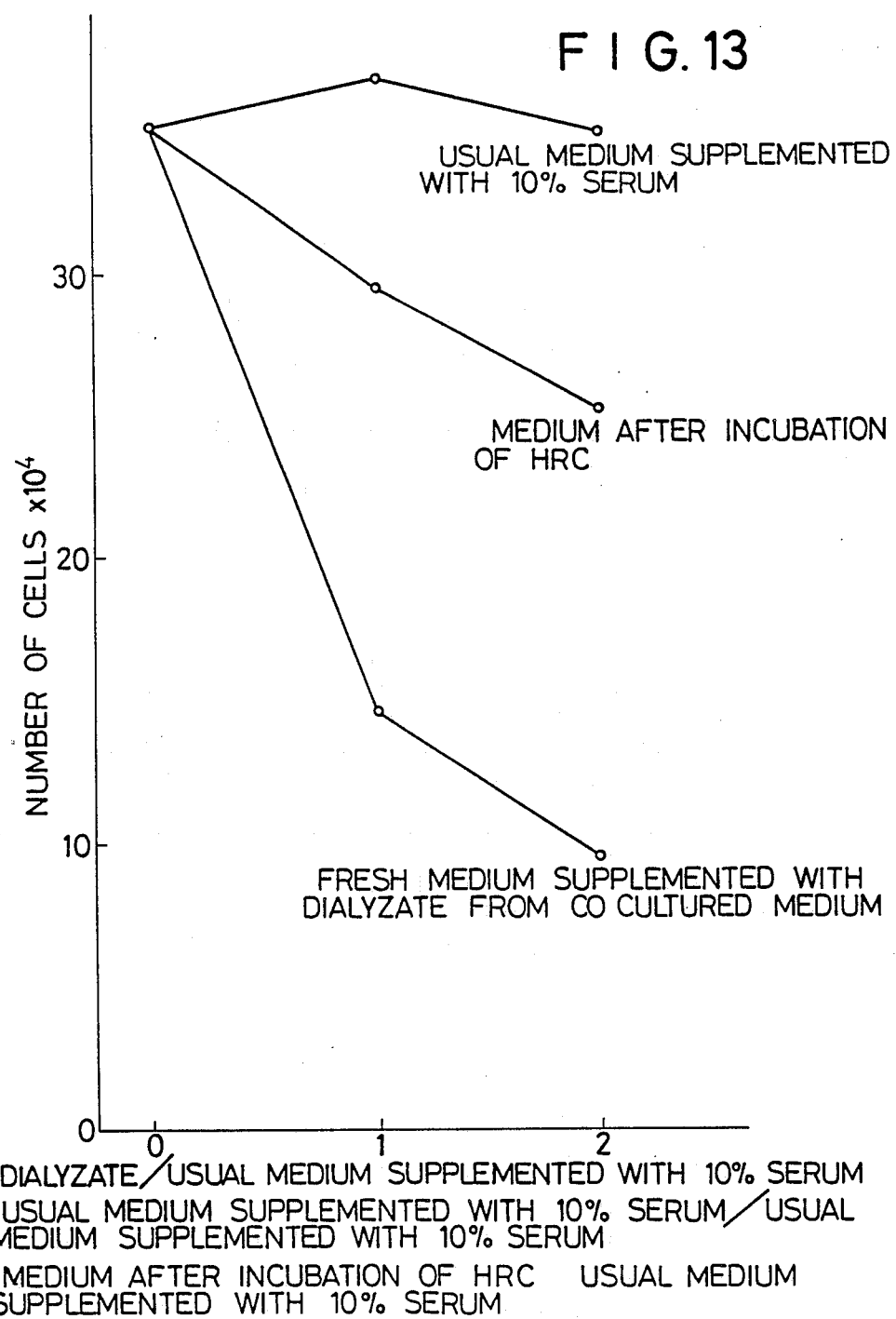
FIG. 13 is a graph showing the proliferation of carcinoma cells in a medium supplemented with a material obtained by dialysis of a co-cultured medium in an extraction medium which contains no serum.

FIG. 13 indicates the variation in HRC cell numbers after 5 days in a medium containing no serum in admixture with, respectively, a mixture of a dialyzate of a co-cultured medium with a usual medium supplemented with 10% serum, with a medium after the incubation of HRC, and with a usual medium supplemented with 10% serum. The results indicate a remarkable inhibitive effect on cell proliferation in the medium supplemented with an extract from the co-cultured medium.

Even if human fibroblasts and tumor cells are not restricted to one type and are present in various forms, similar effects may be effected. With varying ratios of normal cells to tumor cells, the strength of the effect may vary. From the results of the experiments set forth hereinabove, it is seen that tumor cells are preferably inoculated in amounts ranging from 10 to 20 million cells with respect to normal cells in amounts ranging from 7 to 10 million cells. For reference, FIGS. 14 and 15 are attached hereto.

Figure 14:
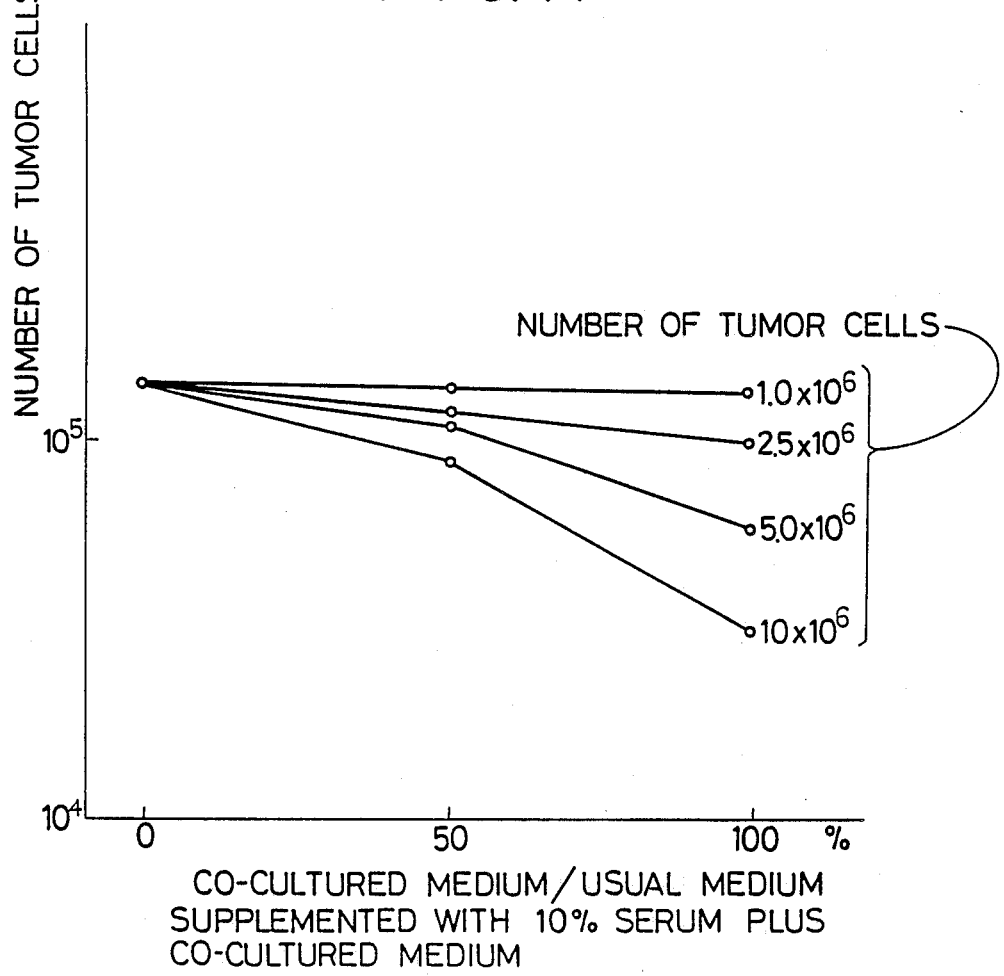
FIG. 14 is a graph showing the proliferation of respective inoculants of carcinoma cells in each of media.

In FIG. 14, the abscissa indicates ratios of co-cultured media to the sum of usual media supplemented with a 10% serum and media for the combined culture, and the ordinate indicates a variation in numbers of tumor cells after 5 days when the number of inoculated carcinoma cells HRC for the combined cultures and of carcinoma cells HRC of the same kind is varied. The results show that the larger the number of inoculated tumor cells or the higher the ratio, the smaller the number of proliferated tumor cells.

Figure 15:
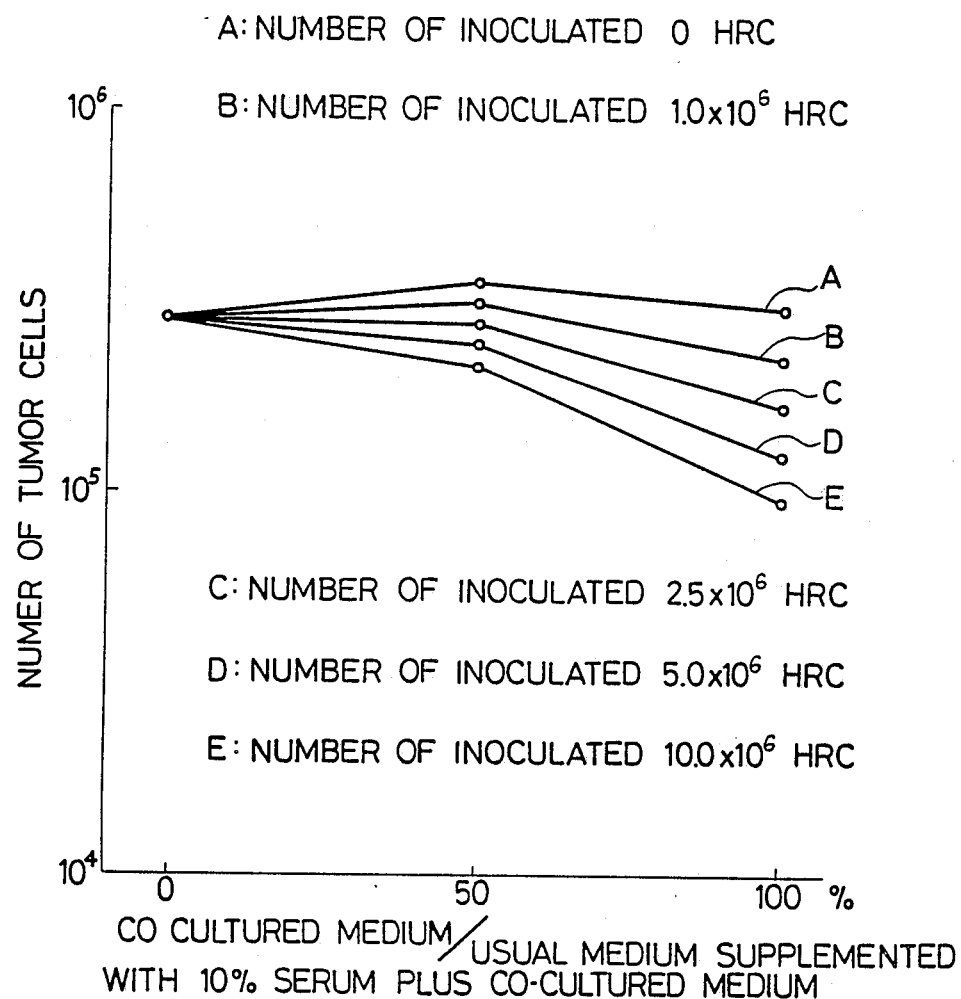
FIG. 15 is a graph showing the proliferation of KB cells in each of media.

In FIG. 15, the abscissa indicates ratios of co-cultured media to the sums of usual media supplemented with 10% serum and co-cultured media, and the ordinate indicates numbers of tumor cells after 5 days when the number of inoculated carcinoma cells KB different from carcinoma cells HRC for the combined culture is varied. Even when different carcinoma cells are used, a tendency similar to that shown in FIG. 14 is seen.

Figure 16:
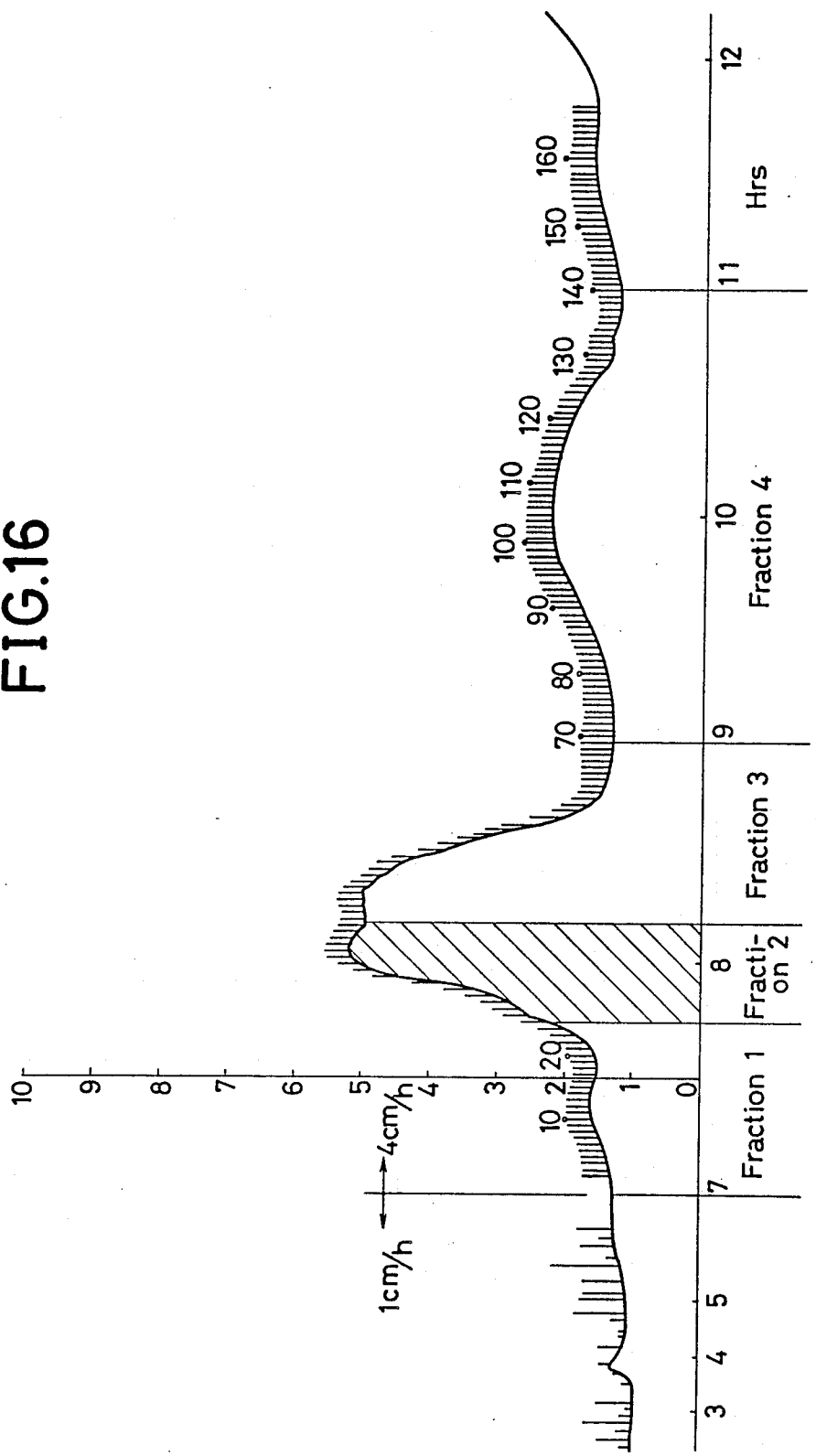
Figure 17:
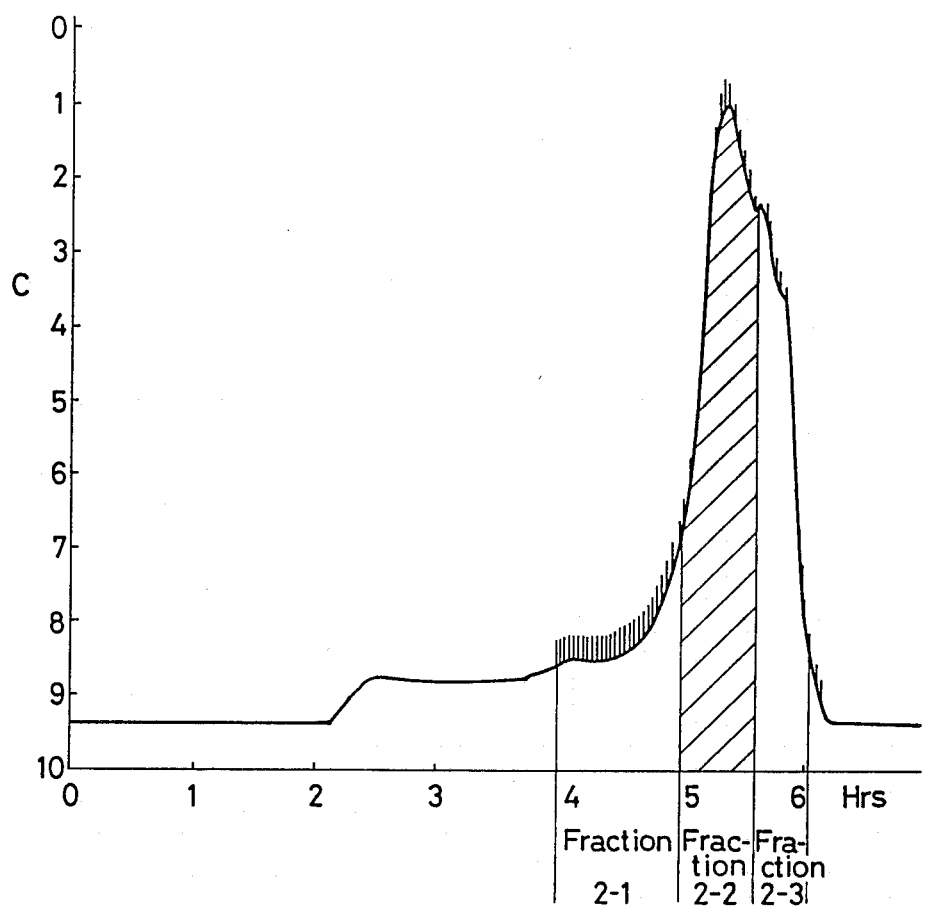

FIG. 16 shows the inhibition activity of Fraction 2 against cancer cells with reference to Table 2;

FIG. 17 shows the absorbance to time of Fractions 2—2 and 2—3; and

Figure 18:
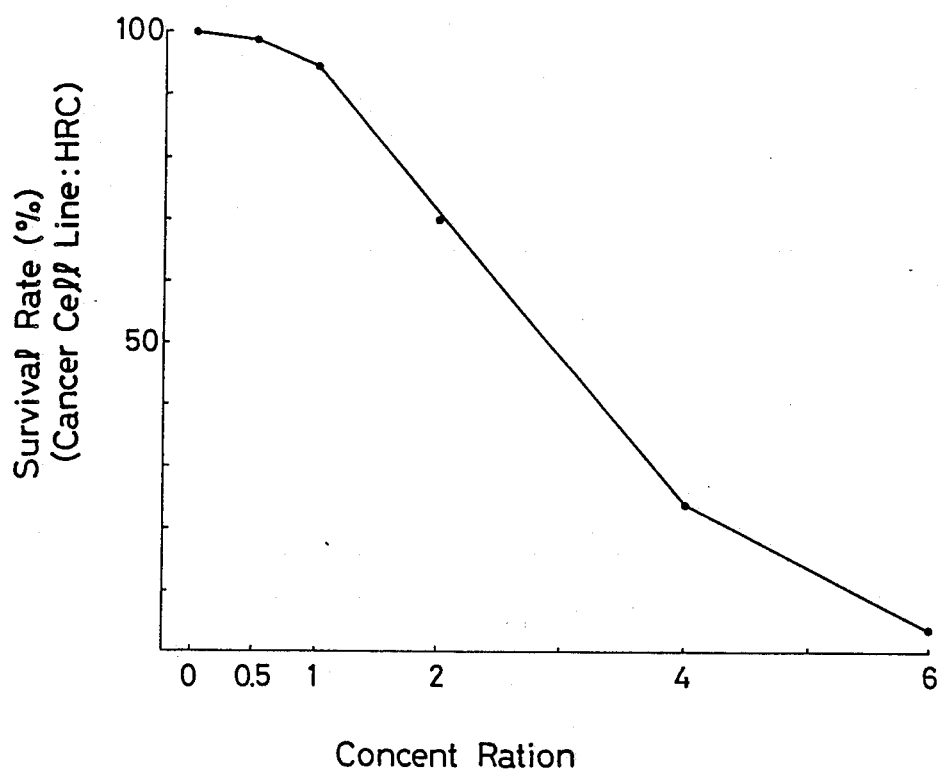

FIG. 18 shows the survival rates of established cells HRC from a human renal carcinoma when concentrations are varied.

The kind of media need not be restricted to BME and may include other media. Concentrations of serum need not be restricted to 10% and may vary, and media without serum also may be employed. Serum may include new born calf serum, cattle serum, calf serum and cattle embryo serum, and serum of other animals may also be used. Cultures may be of standing or settled culture type and of float culture type. Various culture vessels may be employed appropriately.

Experiment 3

(1) Procedure of fractioning

After the cultivation in Experiment 1, 2000 ml of the culture medium were collected, and the collected medium was dissolved in 200 ml of a 0.025 mole NaCl solution as a solvent to dilute it ten times as much as a concentration of the original solution. Next, the diluted solution was expanded with the same solvent solution and was further caused to pass through a 100-mm-diameter and 1000-mm-length column (trade name Biogel P-2, Bio-Rad Laboratory in U.S.A.) which was charged with polyacrylamide in order to carry out a gel filtration.

An amount of the tested sample was 300 ml and an ultraviolet detector was used to measure an absorbance at a wave length of 254 nm.

The absorbance to time is shown in FIG. 16, and a region of 7 to 7¾ hours in the drawing was named fraction 1; a region of 7¾ to 8 3/16 hours fraction 2; a region of 8 3/16 to 9 hours fraction 3; and a region of 9 to 11 hours fraction 4.

Afterward, the culture medium in the region of fraction 2 was further freeze-dried and was then dissolved in redistilled water to dilute it ten times as much as a concentration of the original solution. This diluted solution was caused to pass through a 40-mm-diameter and 1000-mm-length column (trade name Biogel P-2, Bio-Rad Laboratory in U.S.A.) which was charged with polyacrylamide together with redistilled water.

An amount of the tested sample was 20 ml and an ultraviolet detector was used to measure an absorbance at a wave length of 254 nm.

The absorbance to time is shown in FIG. 17, and a region of 4 to 5 hours in the drawing was named fraction 2—1; a region of 5 to 5 9/16 hours fraction 2—2; and a region of 5 9/16 to 6 1/16 hours fraction 2—3.

(2) Experimental procedure for proliferative inhibition of malignant tumor cells In this experiment, there were used established cells HRC originated from a human renal carcinoma, normal human diploid skin fibroblasts, a fresh medium as a control, and an untreated conditioned medium (CMHRC) which was prepared by adding the same amino acids, vitamins and glucose as in the above-mentioned fresh medium to an original culture medium (CMHRC) in the same amounts as in the fresh medium. Fractions 1, 2, 3 and 4 were each concentrated five-fold. Influences of these fractions on the cancer cells and normal cells were compared with the above-mentioned fresh medium and untreated conditioned medium. Obtained results are set forth in Table 2.

In like manner, established cells HRC originated from a human renal carcinoma and normal human diploid skin fibroblasts were used, and a fresh medium was employed as a control. Fractions 2, 2—1, 2—2 and 2—3 were each concentrated five times as much as a concentration of the original culture medium (CMHRC). Influences of these fractions on the cancer cells and normal cells were compared with the above-mentioned fresh medium. Obtained results are set forth in Table 3.

In these tables, an initial cell density was $1 \times 10^4$ cells/plate. In the cases of the respective experimental groups, medium change was carried out every other day, and the number of vital cells was measured on the eighth day. Further, a survival rate of the vital cells to the control, in which cultivation was accomplished in the fresh medium, was represented by percentage.

(3) Experimental results

In Table 2, the noticeable inhibition effect of fraction 2 in FIG. 16 against the cancer cells is described. In Table 3, fraction 2—2 shows the remarkable inhibition results against the cancer cells. It will further be noticed that the normal cells in this region are not so inhibited.

Therefore, it will be understood that in the culture medium of fraction 2—2, there is a concentrated matter which does not much act on the normal cells but which has a remarkable inhibiting effect on the cancer cells.

FIG. 18 shows survival rates (%) of the established cells HRC originated from a human renal carcinoma in fraction 2—2 when its concentrations were varied. The results in this drawing indicate that as the concentrations of fraction 2—2 increase, the survival rates of the cancer cells decrease.

TABLE 2

| Culture | Cancer cells (Cell line, HRC) | | Normal cells (Human diploid skin fibroblasts) | |
|---|---|---|---|---|
| | Cell count $\times 10^4$ cells/plate | Survival rate % | Cell count $\times 10^4$ cells/plate | Survival rate % |
| Fresh medium (control) | 29.3 | 100.0 | 14.7 | 100.0 |
| Untreated conditioned medium (CMHRC) | 1.5 | 5.0 | 3.4 | 23.2 |
| Fraction 1 | 17.1 | 58.5 | 11.5 | 78.4 |
| Fraction 2 | 2.3 | 7.9 | 6.0 | 40.7 |
| Fraction 3 | 22.7 | 77.4 | 13.6 | 92.7 |
| Fraction 4 | 28.8 | 98.2 | 14.6 | 99.4 |

TABLE 3

| Culture | Cancer cells (cell line; HRC) | | Normal cells (Human diploid skin fibroblasts) | |
|---|---|---|---|---|
| | Cell count $\times 10^4$ cells/plate | Survival rate % | Cell count $\times 10^4$ cells/plate | Survival rate % |
| Fresh medium (control) | 35.7 | 100.0 | 17.2 | 100.0 |
| Fraction 2 | 3.3 | 9.3 | 5.1 | 29.8 |
| Fraction 2-1 | 28.5 | 79.8 | 15.9 | 92.2 |
| Fraction 2-2 | 4.1 | 11.4 | 12.5 | 72.6 |
| Fraction 2-3 | 30.6 | 85.8 | 17.0 | 98.8 |

In order to examine the efficacy of this agent for inhibiting the proliferation of tumor in animals, the following three investigations were carried out.

In one experiment, the examination on the rate of life span extension, the agent of this invention was administered into the peritoneum when cancer cells were intraperitoneally transplanted (hereinafter referred to as i.p.-i.p. series, abbreviated from intraperitoneal transplantation).

In a further experiment, the agent of the invention was administered into the peritoneum when cancer cells were subcutaneously transplanted (hereinafter mentioned as s.c.-i.p. series, abbreviated from subcutaneous transplantation.)

In a further experiment, the agent of the invention was injected into the peritoneum when cancer cells were intramuscularly transplanted (hereinafter mentioned as i.m.-i.p series, abbreviated from intramuscular transplantation).

EXAMPLES 4-6

Materials, Methods and Results

Strain of experimented mice: C57BL
Cancer cells used for transplantation Lewis Lung Carcinoma (L.L.C.)
Inoculum size; $10^6$ cells/mouse

EXAMPLE 4

Examination on the rate of life span extension

The cancer cells, which are Lewis Lung Carcinoma cells (L.L.C.) were transplanted in the amount of $10^6$ cells/mouse into the peritonia of two different groups of mice (C57BL series,) two control and the other two experimental. After 48 hours, 1 ml of Eagle's MEM was administered into the peritonia of control group mice, in the amount of 1 cc once a day, and 0.25 ml of 100 times concentrated original agent for inhibiting proliferation of human malignant tumor cells (obtained by culturing said human malignant tumor cells in a medium and then removing said malignant tumor cells from said medium by extraction) with 0.75 ml of Eagle's MEM, making a total of 1 ml, was administered into the peritonia of experimental group mice, in the amount of 1 cc once a day. The administration was done for nine times and after that, it was stopped, and the development was observed.

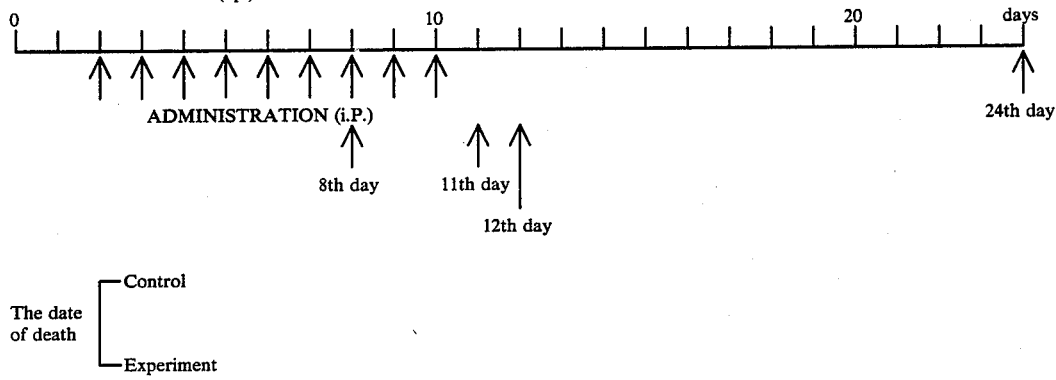

The rate of life sapn extension $= \frac{12 + 24}{8 + 11} \times 100 = 189\ (\%)$

EXAMPLE 5

Examination of inhibiting proliferation of Tumor

The cancer cells, which are Lewis Lung Carcinoma (L.L.C) were transplanted with the amount of $10^6$ cells/mouse under the skin of five control mice and six experimental mice (both belonging to C57BL series). After 24 hours, the anti-tumor agent of the present invention and Eagle's MEM adjusted as 1. were administered into the peritonia of mice in each group for total of 18 times within 14 days. On the 15th day after the transplantation, the mice were killed and both the weight of the mice and the weight of tumors were measured.

(a) The experimental group of mice demonstrated inhibition in the increase of the weight of tumor

|   | (CONTROL) | | (ADMINISTERED) | |
|---|---|---|---|---|
|   | Weight (g) | Weight of Tumor | Weight (g) | Weight of Tumor |
| 1 | 20.30 | 4.40 | 19.90 | 2.75 |
| 2 | 20.50 | 3.70 | 19.50 | 2.00 |
| 3 | 19.65 | 5.40 | 21.70 | 3.20 |
| 4 | 22.00 | 6.25 | 21.95 | 3.65 |
| 5 | 21.35 | 4.75 | 20.15 | 2.00 |
| MEAN | 20.76 | 4.90 | 20.64 | 2.72 |
|   | 0.82 | 0.87 | 0.99 | 0.65 |

From this table, the inhibition in the weight of tumor of the experimental group is clearly recognized.

(b) The Cured—1 mouse

The transplanted tumor started to harden and shrink 10 days after the transplantation, and after 14 days, the mouse was killed. When this mouse was pathologically examined, most of its tumor was completely damaged from bleeding and 3 small lumps of tumor (1 to 2 mm in diameter) were discovered.

EXAMPLE 6

Examination of Metostasis Inhibition

Cancer cells, which are Lewis Lung Carcinoma (L.L.C.) were transplanted in the amount of $10^6$ cells/mouse into the muscles of left thighs of three controlled mice and three administered mice, both belonging to C57BL series. After 24 hours, the anti-tumor agent of the present invention and Eagles's MEM adjusted as 1. and 2. were again administered into the peritonia of mice in each group for total of 14 times within 14 days. On the 15th day after the administration, the mice were killed in order to measure the number of lung metastasis and the weight of their lungs. However, the left hind legs in which the L.L.C. was transplanted, were amputated.

|   | (CONTROL) | (EXPERIMENTAL) |
|---|---|---|
|   | (a) Measurement of metastasis | |
| 1 | 99 | 70 |
| 2 | 78 | 48 |
| 3 | 62 | 44 |
| MEAN | 79.6 | 54.0 |
|   | 15.1 | 11.4 |

The rate of inhibition =

$$\left(1 - \frac{\text{the number of metastasis of adm.}}{\text{the number of metastasis of contr.}}\right) \times 100$$

|   | (b) Measurement of the weight of lung (g) | |
|---|---|---|
| 1 | 0.66 | 0.38 |
| 2 | 0.65 | 0.50 |
| 3 | 0.46 | 0.46 |
| MEAN | 0.59 | 0.47 |
|   | 0.09 | 0.05 |

The weight of lung of administered group is less than the one of control group.

The results of Example 4 show that the rate of life span extension exceeds 130% in i.p.-i.p. series.

Example 5 indicates that the subcutaneous transplanted tumor can be cured or inhibited by administering the agent of the present invention into the peritonia of mice.

Example 6 indicates that the metastasis of tumors can be inhibited by administering this agent into the peritonia of mice.

The most important aspect of the above mentioned experiments is not the direct administration into the transplanted part of a tumor, but rather the fact that the effect can be recognized even by remote administration from peritonia. It is also affirmed that the agent of the invention for inhibiting proliferation of tumor does not exert a harmful influence upon an individual in the experimental group, thus meeting the fundamental conditions of a medicine for safety and efficacy.

What is claimed is:

1. An agent for inhibiting the proliferation of human malignant tumor cells, said agent being produced by culturing said human malignant tumor cells at 37° C. for 3 or 4 days in a growth medium comprising a synthetic medium supplemented with new born calf serum, permitting said malignant tumor cells to proliferate in said growth medium until the growth medium is saturated with the malignant tumor cells, washing the medium to remove the serum, incubating in an extraction medium which does not contain calf serum, and thereafter removing said malignant tumor cells, removing of said malignant tumor cells being conducted by passing said tumor cells through a molecular sieve capable of filtering a substance having a molecular weight of not less than 500, and recovering the agent which inhibits proliferation of human tumor malignant cells.

2. The agent of claim 1, wherein
the human malignant tumor cells are selected from the group consisting of established cell lines originating from a human renal carcinoma, a human gastric carcinoma, a human lung carcinoma, a carcinoma from a human oral cavity and a human myogenic sarcoma.

3. An agent according to claim 1, wherein
the cells are cultured in a growth medium comprising a synthetic medium supplemented with 10% new born calf serum.

4. An agent according to claim 3, wherein
said synthetic medium is Basal Medium Eagle.

5. An agent according to claim 1, wherein
the cells are cultured in a growth medium comprising a synthetic medium supplemented with 5% new born calf serum.

6. An agent according to claim 5, wherein
said synthetic medium is RPMI1640.

7. The agent of claim 1, wherein
said extraction medium is a synthetic medium.

8. The agent of claim 1, wherein
said synthetic medium is Basal Medium Eagle.

9. The agent of claim 1, wherein
the tumor cells are co-cultured with human normal fibroblasts, and further comprising
removing said malignant tumor cells by extraction from a co-cultured medium.

10. The agent of claim 9, wherein
the co-culturing step is carried out in a medium comprising a synthetic medium supplemented with 10% new born calf serum.

11. The agent of claim 9, wherein
said normal fibroblasts are normal diploid skin fibroblasts.

12. The agent of claim 10, wherein
said synthetic medium is Basal Eagle Medium.

* * * * *

Disclaimer 4,963,358—*Tomoyuki Tajima*, Ichikawa, Japan. AGENT FOR INHIBITING PROLIFERATION OF HUMAN MALIGNANT TUMOR CELLS. Patent dated Oct. 16, 1990. Disclaimer filed May 21, 1991, by the assignee, Koken Ltd.

The term of this patent subsequent to March 7, 2006, has been disclaimed.
*[Official Gazette December 17, 1991]*